(12) United States Patent
Bagaoisan

(10) Patent No.: US 7,377,931 B2
(45) Date of Patent: May 27, 2008

(54) BALLOON CATHETER WITH SELF-ACTUATING PURGING VALVE

(75) Inventor: Celso J. Bagaoisan, Union City, CA (US)

(73) Assignee: Medtronic Vascular, Inc, Santa Rosa, CA (US)

( * ) Notice: Subject to any disclaimer, the term of this patent is extended or adjusted under 35 U.S.C. 154(b) by 433 days.

(21) Appl. No.: 10/916,165

(22) Filed: Aug. 11, 2004

(65) Prior Publication Data
US 2006/0036275 A1  Feb. 16, 2006

(51) Int. Cl.
*A61M 29/00* (2006.01)
(52) U.S. Cl. .................................. 606/192; 604/96.01
(58) Field of Classification Search .. 604/97.01–99.04, 604/118, 129, 915, 920, 96.01; 606/191, 606/192
See application file for complete search history.

(56) References Cited

U.S. PATENT DOCUMENTS

| | | | |
|---|---|---|---|
| 4,130,119 A * | 12/1978 | Sessions et al. | 606/195 |
| 4,413,989 A | 11/1983 | Schjeldahl et al. | |
| 4,692,200 A | 9/1987 | Powell | |
| 4,811,737 A | 3/1989 | Rydell | |
| 4,813,934 A * | 3/1989 | Engelson et al. | 604/99.02 |
| 4,848,344 A | 7/1989 | Sos et al. | |
| 5,049,130 A | 9/1991 | Powell | |
| 5,098,393 A * | 3/1992 | Amplatz et al. | 604/167.03 |
| 5,141,518 A * | 8/1992 | Hess et al. | 606/194 |
| 5,176,698 A * | 1/1993 | Burns et al. | 606/192 |
| 5,304,198 A * | 4/1994 | Samson | 606/194 |
| RE34,633 E | 6/1994 | Sos et al. | |
| 5,454,788 A | 10/1995 | Walker et al. | |
| 5,531,689 A | 7/1996 | Burns et al. | |
| 5,728,065 A * | 3/1998 | Follmer et al. | 604/96.01 |
| 6,090,083 A * | 7/2000 | Sell et al. | 604/249 |
| 6,102,891 A | 8/2000 | Maria van Erp | |
| 6,176,843 B1 | 1/2001 | DiCaprio et al. | |
| 2005/0131344 A1 * | 6/2005 | Godaire | 604/99.04 |

FOREIGN PATENT DOCUMENTS

EP  1118348  7/2001
WO  WO 94/27668  12/1994

* cited by examiner

*Primary Examiner*—Nicholas Lucchesi
*Assistant Examiner*—Theodore J. Stigell
(74) *Attorney, Agent, or Firm*—James F. Crittenden

(57) ABSTRACT

A system for treating a vascular condition comprises a catheter having at least one lumen, a stem received within a distal portion of the lumen, a sealing member positioned on the stem, and a balloon operably attached to a distal portion of the catheter. The stem includes a proximal body portion, a sealing portion, and a shoulder portion. The sealing member is movable with hydrodynamic force from an initial air-release position on the proximal body portion of the stem to a sealed position on the sealing portion of the stem. A method for purging a balloon catheter prior to use comprises injecting a liquid into a proximal end of a balloon catheter lumen. The injected liquid forces air through a gap between the lumen wall and a sealing member. The liquid then contacts the sealing member and repositions it to a sealed position.

17 Claims, 5 Drawing Sheets

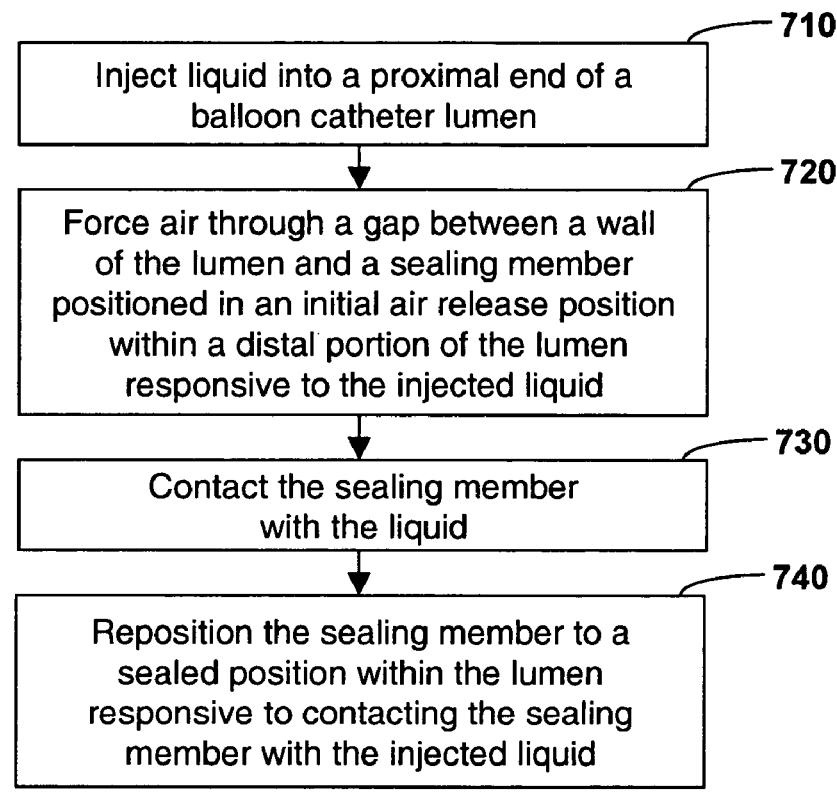

BALLOON CATHETER WITH SELF-ACTUATING PURGING VALVE

TECHNICAL FIELD

This invention relates generally to biomedical devices that are used for treating vascular conditions. More specifically, the invention relates to a balloon catheter with a self-actuating purging valve.

BACKGROUND OF THE INVENTION

Balloon catheters are conventionally used in a wide variety of medical procedures. For example, a balloon is inflated during percutaneous transluminal coronary angioplasty (PTCA) to dilate a stenotic blood vessel and may also be used to deliver a stent to support the vessel lumen in an open position. In addition, the distal end of a guidewire is sometimes equipped with at least one inflatable balloon to provide temporary occlusion of a vessel or to anchor the guidewire within a vessel. An occlusion guidewire can be used to prevent debris generated during vessel treatment from moving with the flowing blood to embolize distally. Anchoring the guidewire helps to prevent the guidewire from being displaced from its position while treatment catheters are advanced or withdrawn over the placed guidewire.

Typically, balloon inflation is accomplished by injecting a liquid under pressure into an inflation lumen of a balloon catheter. However, before the catheter is used, air must be purged from the inflation lumen and the balloon itself to eliminate the risk of an air embolism entering a vessel if the system were to leak or the balloon were to rupture. The air also must be evacuated from the balloon to accomplish a desired inflation of the balloon using a specific volume of liquid without the need to account for compression of an unknown volume of air within the balloon.

A common method of purging a balloon catheter prior to use involves connecting a syringe to the proximal end of the inflation lumen and drawing out as much air as possible. Liquid is then injected into the catheter while the balloon is held vertically to allow the remaining air within the catheter to rise through the inflation liquid towards an inflation port. Liquid and some air bubbles are withdrawn from the catheter, and liquid is again injected. These steps may have to be repeated multiple times to adequately purge the catheter, requiring a substantial amount of preparation time. Therefore, it would be desirable to provide a balloon catheter that overcomes the aforementioned and other disadvantages.

SUMMARY OF THE INVENTION

One aspect of the present invention is a system for treating a vascular condition, comprising a catheter having at least one lumen extending through the catheter, a stem received within a distal portion of the catheter lumen, a sealing member positioned on the stem, and an inflatable balloon operably attached to a distal portion of the catheter. The stem includes a proximal body portion, a sealing portion distal to the body portion, and a shoulder portion distal to the sealing portion. The sealing member is movable with hydrodynamic force from an initial air-release position on the proximal body portion of the stem to a sealed position on the sealing portion of the stem.

The present invention includes another system for treating a vascular condition that comprises a hypotube, a core wire, self-actuating means for allowing air to be purged from the hypotube and for preventing air from re-entering the hypotube through the distal end of the hypotube, and an inflatable balloon operably attached to a distal portion of the hypotube.

Another aspect of the present invention is a method for purging a balloon catheter prior to use. Liquid is injected into a proximal end of a balloon catheter lumen. In response to the injected liquid, air is forced through a gap between the lumen wall and a sealing member in an initial air-release position within the lumen. The sealing member is contacted with the injected liquid, and, in response, is repositioned to a sealed position within the lumen.

The aforementioned and other features and advantages of the invention will become further apparent from the following detailed description of the presently preferred embodiments, read in conjunction with the accompanying drawings, which are not to scale. The detailed description and drawings are merely illustrative of the invention rather than limiting, the scope of the invention being defined by the appended claims and equivalents thereof.

BRIEF DESCRIPTION OF THE DRAWINGS

FIG. 7 is a flow diagram of one embodiment of a method for purging a balloon catheter prior to use, in accordance with the present invention.

DETAILED DESCRIPTION OF THE PRESENTLY PREFERRED EMBODIMENTS

Figure 1:
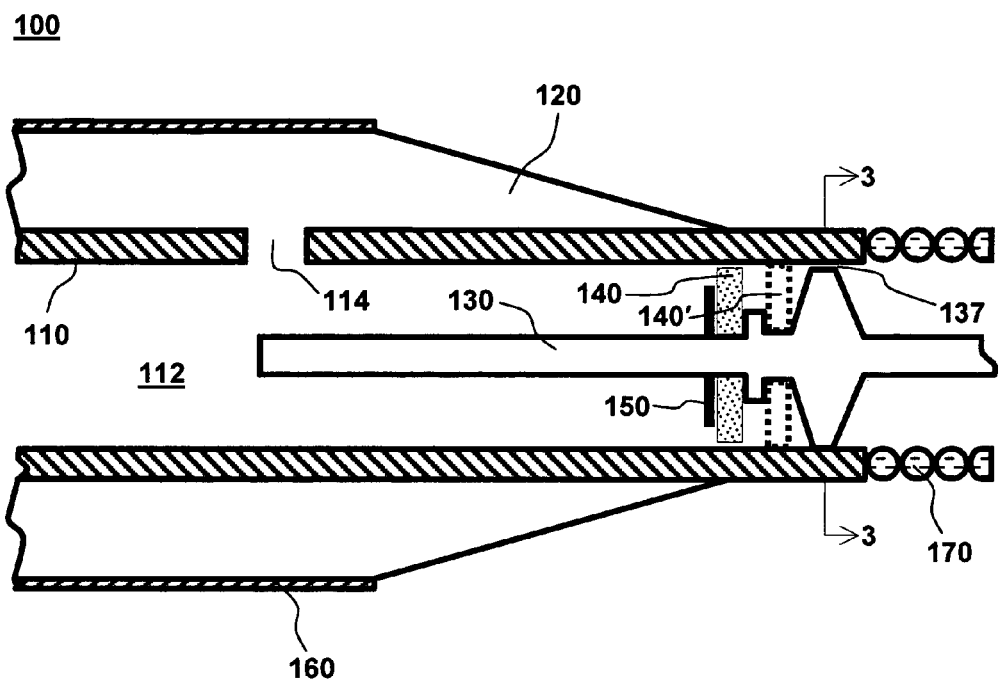
FIG. 1 is an illustration of one embodiment of a system for treating a vascular condition, in accordance with the present invention.

One aspect of the present invention is a system for treating a vascular condition. One embodiment of the system, in accordance with the present invention, is illustrated at 100 in FIGS. 1-3. Like elements share like reference numbers in these figures. System 100 comprises catheter 110, balloon 120, stem 130, sealing member 140, retaining member 150, sheath 160, and coil 170. Lumen 112 extends through catheter 110. Inflation port 114 opens from lumen 112 into the interior of balloon 120. Stem 130 includes proximal body portion 132, sealing portion 134, shoulder portion 136, and distal body portion 138. As used herein, the terms "proximal" and "distal" are with reference to the treating clinician during deployment of the device, wherein a distal end or distal direction are away from the clinician and a proximal end or proximal direction are toward or near the clinician. Sealing portion 134 further comprises stop section 133 and seat section 135. Shoulder portion 136 includes air-release opening 137. Although described below in the context of an occlusion guidewire, system 100 may be readily adapted to a wide variety of balloon catheters, including those having additional functionalities, structures, or intended uses.

Catheter 110 is made of an appropriate biocompatible material such as stainless steel or nitinol. Where catheter 110 is to be used as a guidewire during a procedure such as a conventional percutaneous transluminal coronary angioplasty involving femoral artery access, catheter 110 may be about 120 centimeters to about 320 centimeters long, with a length of about 180 centimeters often being used for a single-operator device and 300 centimeters for over-the-wire applications. The outer diameter of the catheter may range from about 0.010 inches to 0.038 inches, and preferably is 0.014 inches or smaller when the catheter is to be used as a guidewire.

In the present embodiment, a single lumen 112 having a constant cross-sectional area extends through catheter 110. In another embodiment, the cross-sectional area of the lumen may vary, or the catheter may include multiple lumens. As shown in FIG. 1, lumen 112 is substantially circular in cross-section. One skilled in the art will appreciate that other cross-sectional shapes are possible, particularly where the catheter includes multiple lumens.

Inflatable balloon 120 is operably attached to a distal portion of catheter 110. Balloon 120 may be made of a biocompatible material such as a thermoplastic polyurethane (TPU) resin, styrene-ethylene-butadiene-styrene (SEBS), PEBAX®, or the like. Balloon 120 is shown compressed (partially compressed for clarity) about catheter 110 using removable sheath 160. Fully compressing the balloon substantially eliminates air from the balloon and also prevents liquid from entering the balloon during purging of the system. Sheath 160 may be, for example, a section of thin-walled tubing that has been heat-shrunk onto balloon 120 after the balloon has been deflated, folded, wrapped, or otherwise manipulated during manufacture to minimize its profile.

Stem 130 is received within a distal portion of lumen 112. In the present embodiment, stem 130 serves not only as part of a self-actuating valve, but also as a support or core wire to ensure the distal end of catheter 110 is not so flexible that it tends to bend back upon itself when advanced through a patient's vasculature. In another embodiment, the stem may not function as a core wire. Stem 130 comprises an appropriate biocompatible material such as nitinol or stainless steel.

Figure 2:
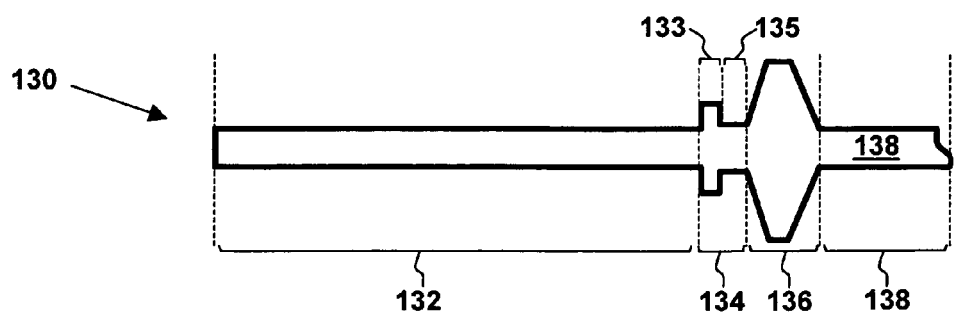
FIG. 2 shows the stem of the system of FIG. 1.

As illustrated in FIG. 2, stem 130 includes proximal body portion 132, sealing portion 134, shoulder portion 136, and distal body portion 138. In the present embodiment, proximal body portion 132 is elongated to provide support for the distal end of catheter 110. Distal body portion 138 is also elongated and extends beyond the distal end of catheter 110. Distal body portion 138 may be shapeable to aid in directing system 100 through the vasculature of a patient. Distal body portion 138 may be tapered, with the cross-sectional area decreasing in a distal direction. Coil 170, illustrated in FIG. 1, surrounds distal body portion 138 and is attached to one or both of distal body portion 138 and a distal portion of catheter 110 by a method such as soldering. Coil 170 is formed of a suitable radiopaque material such as gold, platinum, or a platinum alloy. One of ordinary skill in the art will appreciate that a system in accordance with the present invention need not include either distal body portion 138 or coil 170.

Sealing portion 134 is distal to proximal body portion 132 and, in the present embodiment, comprises two sections: proximal stop section 133 and distal seat section 135. In the present embodiment, both stop section 133 and seat section 135 have cross-sectional areas greater than that of proximal body portion 132, with the cross-sectional area of stop section 133 being greater than that of seat section 135.

Figure 3:
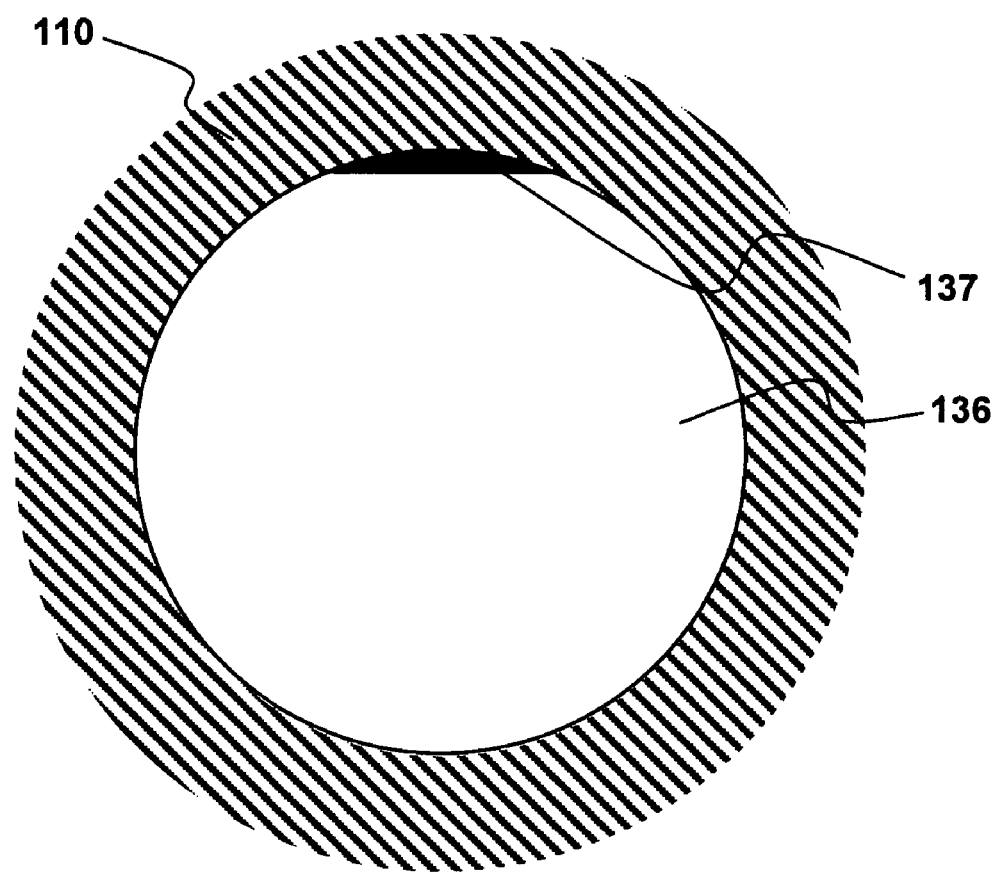
FIG. 3 is an enlarged cross-sectional view taken along line 3-3 of FIG. 1, showing an air-release opening of the system.

As best seen in FIG. 3, which is an enlarged cross-sectional view of system 100, shoulder portion 136 is substantially circular in cross-section and fits snugly within lumen 112. Shoulder portion 136 acts to center stem 130 within catheter 110 and is the portion of stem 130 to which catheter 110 is attached, using one or more methods such as swaging, crimping, soldering, bonding with an adhesive, and the like. Where lumen 112 is not circular in cross-section, the shape of shoulder portion 136 would be complementary to that of lumen 112. Shoulder portion 136 is preferably formed as an integral part of stem 130 prior to positioning stem 130 within catheter 110 during manufacture. However, shoulder portion 136 may also be formed after stem 130 has been received within catheter lumen 112, for example by soldering stem 130 within lumen 112, with the solder forming shoulder portion 136.

As seen in FIG. 3, an outer edge of shoulder portion 136 is flattened to form air-release opening 137 between the outer edge of shoulder portion 136 and the wall of catheter lumen 112. One skilled in the art will appreciate that air-release opening 137 may take a variety of forms, including a notch or groove formed in the outer edge of shoulder portion 136, a hole drilled or otherwise formed longitudinally through shoulder portion 136, or even a hole formed in a distal portion of the wall of catheter 110, the hole passing radially outward through the wall of catheter 110 immediately proximal to shoulder portion 136. One or more air-release openings may be formed simply as a function of gaps remaining between the outer surface of shoulder portion 136 and the wall of catheter lumen 112 when catheter 110 is swaged or crimped onto shoulder portion 136.

Sealing member 140 is positioned on stem 130. In the present embodiment, sealing member 140 is an O-ring that fits loosely on proximal portion 132 of stem 130 when the sealing member is in its initial air-release position, shown at 140 in FIG. 1. Other sealing member shapes are possible. Retaining member 150 is affixed to stem 130 to prevent sealing member 140 from moving proximally on the stem. A retaining member may not be required in other embodiments. Sealing member 140 is dimensioned to have a diameter slightly smaller than that of lumen 112 when the sealing member is positioned on proximal portion 132, forming a gap between the wall of lumen 112 and the outer edge of sealing member 140 that provides adequate clearance for air to pass but allows little or no liquid to pass.

When a liquid such as a radiographic contrast solution is injected into the proximal end of lumen 112, air within the lumen is forced to flow in a distal direction, past sealing member 140, and out through air-release opening 137. Once all of the air is purged and the liquid reaches sealing member 140, all or most of the liquid is stopped by the sealing member. As liquid continues to be injected, pressure builds up within lumen 112, and the resulting hydrodynamic force moves sealing member 140 from its initial air-release position on the proximal body portion of the stem to a sealed position on the sealing portion of the stem, shown in phantom at 140' in FIG. 1.

As noted above, in the present embodiment, sealing portion 134 comprises proximal stop section 133 and distal seat section 135. The advancing liquid pushes sealing member 140 up and over stop section 133 and onto seat section 135, as shown in FIG. 1. Shoulder section 136 of stem 130 prevents sealing member 140 from advancing farther distally. Stop section 133 is sized to prevent sealing member 140 from moving in a proximal direction once the hydrodynamic force is withdrawn, and whenever a partial vacuum is applied to lumen 112 to deflate balloon 120.

Because seat section 135 has a larger cross-sectional area than does proximal body portion 132, the sealing member, which initially fit loosely on proximal body portion 132, now fits securely on seat section 135 and is deformed radially outward from stem 130 so that the outer edge of sealing member 140' is pressed against the wall of lumen 112, sealing the distal end of the lumen. The sealing member may carry a lubricant such as a grease or silicone to fill any voids or surface imperfections in the wall of lumen 112 that would prevent the sealing member from fully sealing against the lumen wall.

In an otherwise similar embodiment, the cross-sectional area of the seat section is no larger than that of the proximal body portion of the stem. Instead, the catheter lumen narrows adjacent to a distal end of the catheter, forming a tight fit for the sealing member once it has moved distal to the stop section of the stem. The narrowed lumen may be accomplished by, for example, swaging the catheter onto the shoulder portion of the stem, at the same time swaging an area of the catheter immediately proximal to the area enclosing the shoulder portion of the stem and corresponding to the position of the seat section of the stem.

Once sealing member 140 is forced over stop section 133 and onto seat section 135, the sealing member is locked in place and becomes a permanent seal so that when a negative pressure is applied, for example to withdraw excess contrast solution prior to using system 100, air is prevented from being aspirated back into the system through its distal end. The system is purged of air and ready for use. A sheath used to compress balloon 120 may now be removed and, once the system is in place within a patient's vasculature, additional contrast solution may be injected to inflate balloon 120 through inflation port 114, which opens from lumen 112 into the interior of balloon 120.

Figure 4:
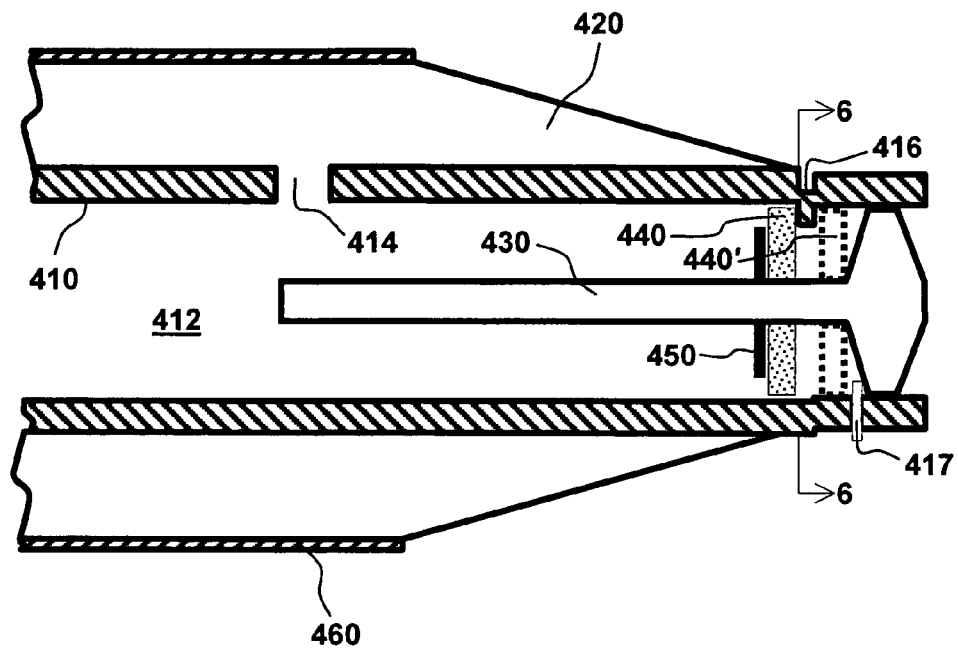
FIG. 4 is an illustration of another embodiment of a system for treating a vascular condition, in accordance with the present invention.
Figure 5:
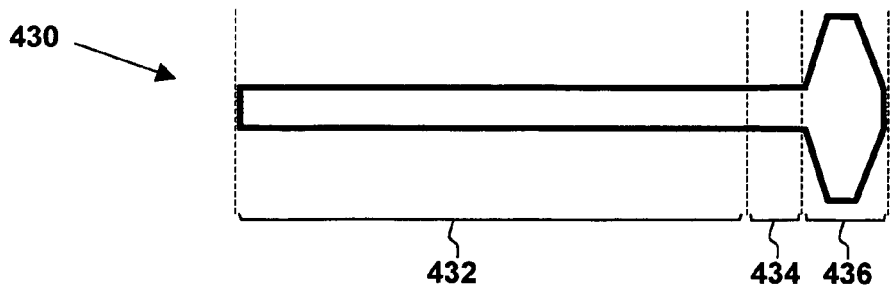
FIG. 5 shows the stem of the system of FIG. 4.
Figure 6:
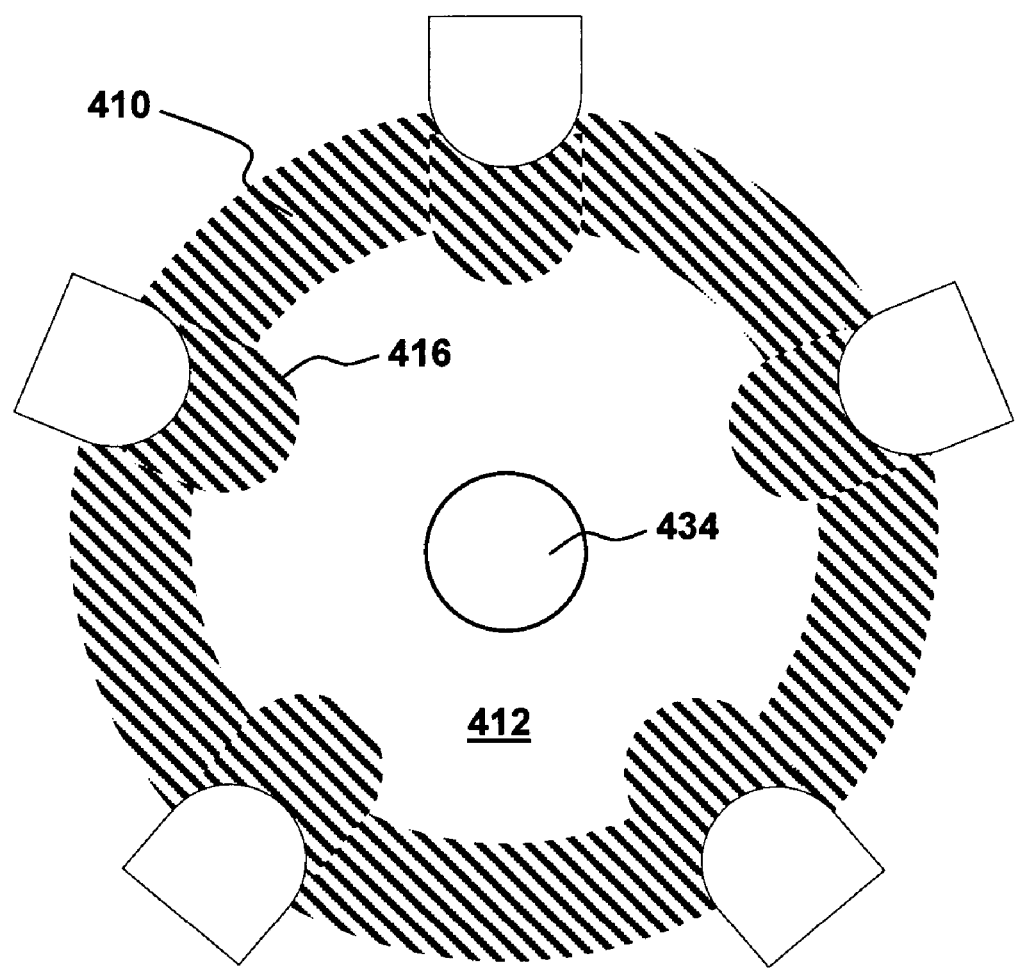
FIG. 6 is an enlarged cross-sectional view taken along line 6-6 of FIG. 4, showing a stop formed in the catheter.

Another embodiment of a system in accordance with the present invention is illustrated in FIGS. 4-6. Like elements share like reference numbers in these figures. System 400 includes catheter 410, balloon 420, stem 430, sealing member 440, and removable sheath 460. Lumen 412 extends through catheter 410. Inflation port 414 opens from lumen 412 into the interior of balloon 420 to allow inflation of the balloon. Stop 416 is formed in catheter 410 and extends into lumen 412. A distal portion of catheter 410 includes air-release opening 417. Stem 430 includes proximal body portion 432, sealing portion 434, and shoulder portion 436.

As illustrated in FIG. 4, catheter 410 is a stainless steel hypotube having a single lumen 412 extending through the catheter. Stop 416 extends into lumen 412 adjacent to the distal end of catheter 410. In the present embodiment, stop 416 is a series of crimped indentations spaced around the circumference of catheter 410. A portion of lumen 412 immediately distal to stop 416 is narrowed, this portion having a cross-sectional area that is less than that of lumen 412 proximal to stop 416 but still greater than the cross-sectional area defined by stop 416. The narrowed lumen may be formed by swaging a distal portion of catheter 410. Air release opening 417 passes radially outward through the wall of catheter 410 distal to stop 416. The opening may be formed by, for example, laser drilling through the wall of catheter 410.

Inflatable balloon 420 is operably attached to a distal portion of catheter 410. Balloon 420 may be made of a biocompatible material such as a thermoplastic polyurethane (TPU) resin, styrene-ethylene-butadiene-styrene (SEBS), PEBAX®, or the like. Balloon 420 is shown compressed (partially compressed for clarity) about the catheter by removable sheath 460. Fully compressing the balloon eliminates air from the balloon and also prevents liquid from entering the balloon during purging of the system. Sheath 460 may be, for example, a section of thin-walled tubing that has been heat-shrunk onto balloon 420 after the balloon has been folded or otherwise manipulated or treated during manufacture to minimize its profile.

Stem 430 is received within a distal portion of lumen 412. Stem 430 comprises an appropriate biocompatible material such as nitinol or stainless steel and includes proximal body portion 432, sealing portion 434, and shoulder portion 436, as best seen in FIG. 5. Catheter 410 is attached to shoulder portion 436 using one or more methods such as swaging, crimping, soldering, bonding with an adhesive, and the like. Shoulder portion 436 may be formed as an integral part of stem 430 prior to positioning stem 430 within catheter 410 during manufacture or may be formed after stem 430 has been received within catheter lumen 412, for example by soldering stem 430 within lumen 412, with the solder forming shoulder portion 436. Stem 430 may optionally include a distal body portion (not shown).

Sealing member 440 is positioned on stem proximal portion 432 when sealing member 440 is in its initial air-release position. Sealing member 440 is dimensioned to have a cross-sectional area slightly smaller than that of lumen 412 when the sealing member is positioned on proximal portion 432, forming a gap between the wall of lumen 412 and the outer edge of sealing member 440 that provides adequate clearance for air to pass but allows little or no liquid to pass.

When a liquid such as a radiographic contrast solution is injected into the proximal end of lumen 412, air within the catheter is forced to flow in a distal direction, past sealing member 440, and out through air-release opening 417. Once all of the air is purged and the liquid reaches sealing member 440, all or most of the liquid is stopped by the sealing member. As liquid continues to be injected, pressure builds up within lumen 412, and the resulting hydrodynamic force moves sealing member 440 from its initial air-release position on the proximal body portion of stem 430 to a sealed position on sealing portion 434, shown in phantom at 440' in FIG. 4. Stem shoulder section 436 prevents sealing member 440 from advancing farther in a distal direction. To reach the sealed position, sealing member 440 passes under catheter stop 416. The number and size of the indentations comprising stop 416 are designed to prevent sealing member 440 from moving in a proximal direction once the hydrodynamic force is withdrawn, and whenever a partial vacuum is applied to lumen 412 to deflate balloon 420. An exemplary arrangement of indentations is shown in FIG. 6, which is an enlarged cross-sectional view of system 400. One skilled in the art will appreciate that the number and size of the indentations may be varied.

The narrowed portion of lumen 412 distal to stop 416 is sized to ensure that the outer edge of sealing member 440 is pressed against the wall of the lumen, thereby sealing the distal end of the lumen. The outer edges of sealing member 440 may carry a lubricant such as a grease or silicone to fill any voids or surface imperfections in the wall of lumen 412 that would prevent sealing member 440 from fully sealing against the lumen wall.

Thus, once sealing member 140 is forced distal to catheter stop 416 and onto sealing portion 434 of stem 430, the sealing member is locked in place and becomes a permanent seal so that when a negative pressure is applied, for example to withdraw excess contrast solution prior to using system 400, air is prevented from being aspirated back into the system through its distal end. The system is purged of air and ready for use. Sheath 460 may now be removed from balloon 420 and, once the system is in place within a patient's vasculature, additional contrast solution may be injected to inflate balloon 420 through inflation port 414, which opens from lumen 412 into the interior of balloon 420.

Another system for treating a vascular condition in accordance with the present invention comprises a hypotube, a core wire, self-actuating means for allowing air to be purged from the hypotube and for preventing air from re-entering the hypotube through the distal end of the hypotube, and an inflatable balloon operably attached to a distal portion of the hypotube. The system may additionally include removable means for compressing the balloon.

The hypotube may be as described above for system 100 and illustrated in FIG. 1 at 110, comprising a biocompatible material such as stainless steel or nitinol. The core wire may be a stem such as is described above and illustrated in FIG. 1 at 130. At least a portion of the core wire is received within a distal portion of the hypotube lumen. A distal portion of the core wire may extend beyond the distal end of the hypotube.

The inflatable balloon operably attached to a distal portion of the hypotube may be as described above and illustrated in FIG. 1 at 120. The optional removable means for compressing the balloon may be a removable sheath such as has been described above and illustrated in FIG. 1 at 160.

The self-actuating means may be a sealing member such as is described above and illustrated in FIG. 1 at 140 positioned on the core wire. When in an initial air-release position as illustrated at 140 in FIG. 1, the sealing member allows air to be purged from the hypotube. The sealing member self-actuates into a sealed position such as is illustrated in phantom at 140' in FIG. 1, preventing air from re-entering the hypotube through the distal end of the hypotube.

Another aspect of the present invention is a method for purging a balloon catheter prior to use. FIG. 7 shows a flow diagram of one embodiment of the method in accordance with the present invention.

Liquid is injected into a proximal end of a balloon catheter lumen (Block 710). In response to the injected liquid, air is forced through a gap between the lumen wall and a sealing member in an initial air-release position within the lumen (Block 720). The sealing member is contacted with the injected liquid (Block 730), and, in response, is repositioned to a sealed position within the lumen (Block 740).

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A system for treating a vascular condition, comprising:
a catheter having at least one lumen extending therethrough;
a stem received within a distal portion of the catheter lumen, the stem including a proximal body portion, a sealing portion distal to the body portion, and a shoulder portion distal to the sealing portion;
a sealing member positioned on the stem, wherein the sealing member is movable with hydrodynamic force from an initial air-release position on the proximal body portion of the stem to a sealed position on the sealing portion of the stem wherein in the air-release position the sealing member allows air in the at least one lumen to be purged out of the distal portion of the lumen and in the sealed position the sealing member prevents air from re-entering the distal portion of the lumen; and
an inflatable balloon operably attached to a distal portion of the catheter.

2. The system of claim 1 further comprising:
a retaining member affixed to the stem proximal to the initial air-release position of the sealing member.

3. The system of claim 1 further comprising:
a removable sheath disposed on the balloon, wherein the sheath compresses the balloon.

4. The system of claim 1 wherein the catheter is attached to the shoulder portion of the stem using at least one method selected from a group consisting of swaging, crimping, soldering, and bonding.

5. The system of claim 1 wherein an air-release opening is formed in one of the shoulder portion of the stem or a distal portion of the catheter.

6. The system of claim 1 wherein the sealing portion of the stem comprises a proximal stop section and a distal seat section, the stop section having a cross-sectional area greater than that of the seat section.

7. The system of claim 6 wherein the stop section has a cross-sectional area greater than that of the proximal body portion of the stem.

8. The system of claim 1 wherein the catheter includes at least one stop extending into the lumen of the catheter adjacent to a distal end of the catheter.

9. The system of claim 8 wherein the catheter stop comprises at least one indentation formed in an external wall of the catheter, the indentation extending into the central lumen.

10. The system of claim 1 wherein the catheter lumen narrows adjacent to a distal end of the catheter.

11. The system of claim 1 wherein the stem includes a distal body portion extending beyond a distal end of the catheter.

12. The system of claim 1 wherein a cross-sectional area of a stem distal body portion decreases in a distal direction.

13. The system of claim 12 further comprising:
a coil surrounding at least a portion of the stem distal body portion.

14. The system of claim 1 wherein the catheter includes at least one inflation port opening from the catheter lumen into an interior of the balloon.

15. The system of claim 1 wherein the stem serves as a core wire.

16. The system of claim 1 wherein the sealing member comprises an 0-ring.

17. The system of claim 1 further comprising:
a lubricant disposed on an outer surface of the sealing member.

* * * * *